United States Patent
LeClair et al.

(10) Patent No.: US 8,156,166 B2
(45) Date of Patent: Apr. 10, 2012

(54) METHOD AND APPARATUS FOR SELECTING A DOCTOR BASED ON AN OBSERVED EXPERIENCE LEVEL

(75) Inventors: Terry LeClair, Fremont, CA (US); Steven A. Sholtis, El Dorado Hills, CA (US)

(73) Assignee: Intuit Inc., Mountain View, CA (US)

( * ) Notice: Subject to any disclaimer, the term of this patent is extended or adjusted under 35 U.S.C. 154(b) by 316 days.

(21) Appl. No.: 11/834,464

(22) Filed: Aug. 6, 2007

(65) Prior Publication Data

US 2009/0043801 A1    Feb. 12, 2009

(51) Int. Cl.
G06F 12/00    (2006.01)
(52) U.S. Cl. ............................................. 707/944; 705/4
(58) Field of Classification Search .................. 707/944; 705/4
See application file for complete search history.

(56) References Cited

U.S. PATENT DOCUMENTS

| | | | |
|---|---|---|---|
| 5,911,687 A * | 6/1999 | Sato et al. ..................... 600/300 |
| 2002/0046075 A1 * | 4/2002 | Gangopadhyay et al. ........ 705/8 |
| 2003/0191668 A1 * | 10/2003 | Oka et al. .......................... 705/2 |
| 2004/0133587 A1 * | 7/2004 | Matsumoto et al. .......... 707/102 |
| 2005/0234968 A1 * | 10/2005 | Arumainayagam et al. .. 707/102 |
| 2006/0100904 A1 * | 5/2006 | Jee et al. ............................. 705/2 |
| 2006/0112086 A1 * | 5/2006 | Douress et al. .................... 707/3 |
| 2006/0161456 A1 * | 7/2006 | Baker et al. ....................... 705/2 |
| 2006/0287970 A1 * | 12/2006 | Chess et al. ....................... 707/1 |
| 2007/0299719 A1 * | 12/2007 | Stolba ............................. 705/11 |
| 2008/0077461 A1 * | 3/2008 | Glick ................................. 705/7 |

FOREIGN PATENT DOCUMENTS

JP    2006293897 A  * 10/2006

OTHER PUBLICATIONS

"Oracle8i Data Warehousing Guide, Release 2 (8.1.6)," Oracle Corporation, 1999.*

* cited by examiner

*Primary Examiner* — Cheyne Ly
(74) *Attorney, Agent, or Firm* — Park, Vaughan, Fleming & Dowler LLP

(57) ABSTRACT

Some embodiments of the present invention provide a system that facilitates the selection of a doctor for a user. The system provides a list of doctors to the user based on an observed experience level of the listed doctors with a condition or a procedure. During operation, the system receives from a user a selection criteria for selecting of a doctor. The system also receives from the user a medical profile for the user. Next, the system receives from a third-party a plurality of doctors' profiles. Then, the system ranks the plurality of doctors' profiles into a ranked list based on the selection criteria and conditions within the medical profile. Finally, the system sends the ranked list to the user.

21 Claims, 2 Drawing Sheets

METHOD AND APPARATUS FOR SELECTING A DOCTOR BASED ON AN OBSERVED EXPERIENCE LEVEL

BACKGROUND

Related Art

When individuals find themselves in need of medical care, they often have difficult time finding a doctor that they will be satisfied with. Many individuals select their doctors based on: a referral from a primary care physician, a recommendation from a friend or relative; or a healthcare provider directory. For example, an individual might go to a healthcare provider's website and search for a doctor based on a specialty and a geographic area. For example, the individual might search for an orthopedic surgeon within ten miles of zip code 95618. Quite often, these individuals end up selecting doctors they are not completely satisfied with, or doctors who do not have the optimal specialty for their specific medical condition.

In order to assist individuals in selecting a doctor, some companies have created specialized services to help in the selection process. However, these specialized services typically only provide a directory that identifies doctors based on simple criteria, such as a geographic location. Worse yet, some of these services rank the doctors based on the amount of money each doctor has paid to the service provider. For example, a doctor who has paid the service provider will be recommended above a doctor who has not paid the service provider.

SUMMARY

Some embodiments of the present invention provide a system that facilitates selecting a doctor based on an observed experience level with a condition or a procedure. During operation, the system receives from a user a selection criteria for selecting of a doctor. The system also receives a medical profile for the user. Next, the system receives from a third-party a plurality of doctors' profiles. Then, the system ranks the plurality of doctors' profiles into a ranked list based on the selection criteria and conditions within the medical profile. Finally, the system sends the ranked list to the user.

In some embodiments of the present invention, the selection criteria can include: a geographic location, an offset from a geographic location, a healthcare plan, a healthcare provider organization, an in-network flag that indicates if a potential doctor is in the user's healthcare network, a time indicator that indicates if a potential doctor is available at the indicated time, a new-patient indicator indicating if a potential doctor is accepting new patients, a satisfaction rating, an amenities rating, a transportation rating, a dispute rating, a procedure cost, a recency rating, and an experience rating.

In some embodiments of the present invention, the medical profile can include: a list of medications used by the user, a history of past procedures for the user, a physical condition of the user, a race of the user, an age of the user, a sex of the user, and a religious affiliation of the user.

In some embodiments of the present invention, each profile in the plurality of doctors' profiles can include: a geographic location, a healthcare plan, a healthcare provider organization, a time indicator that indicates when a doctor is available, a new-patient indicator indicating if a doctor is accepting new patients, a satisfaction rating, an amenities rating, a transportation rating, a dispute rating, a recency rating, a procedure cost, and an experience rating.

In some embodiments of the present invention, the third-party can include: a patient, an insurance company, a healthcare organization, a professional organization, a government, and any organization that collects statistical information.

In some embodiments of the present invention, the plurality of doctors' profiles are stored in a database.

In some embodiments of the present invention, the plurality of doctors' profiles are stored using a star schema.

In some embodiments of the present invention, the system filters the ranked list based on at least one of the selection criteria and the medical profile.

In some embodiments of the present invention, the system receives from the user a designation of a profile from the plurality of doctors' profiles. The system then sends the user additional information about a doctor associated with the profile.

In some embodiments of the present invention, the doctor can include one of: a medical doctor, a dentist, an optometrist, a therapist, a chiropractor, and anyone else who provides healthcare services to the user within the medical field.

DETAILED DESCRIPTION

Figure 1:
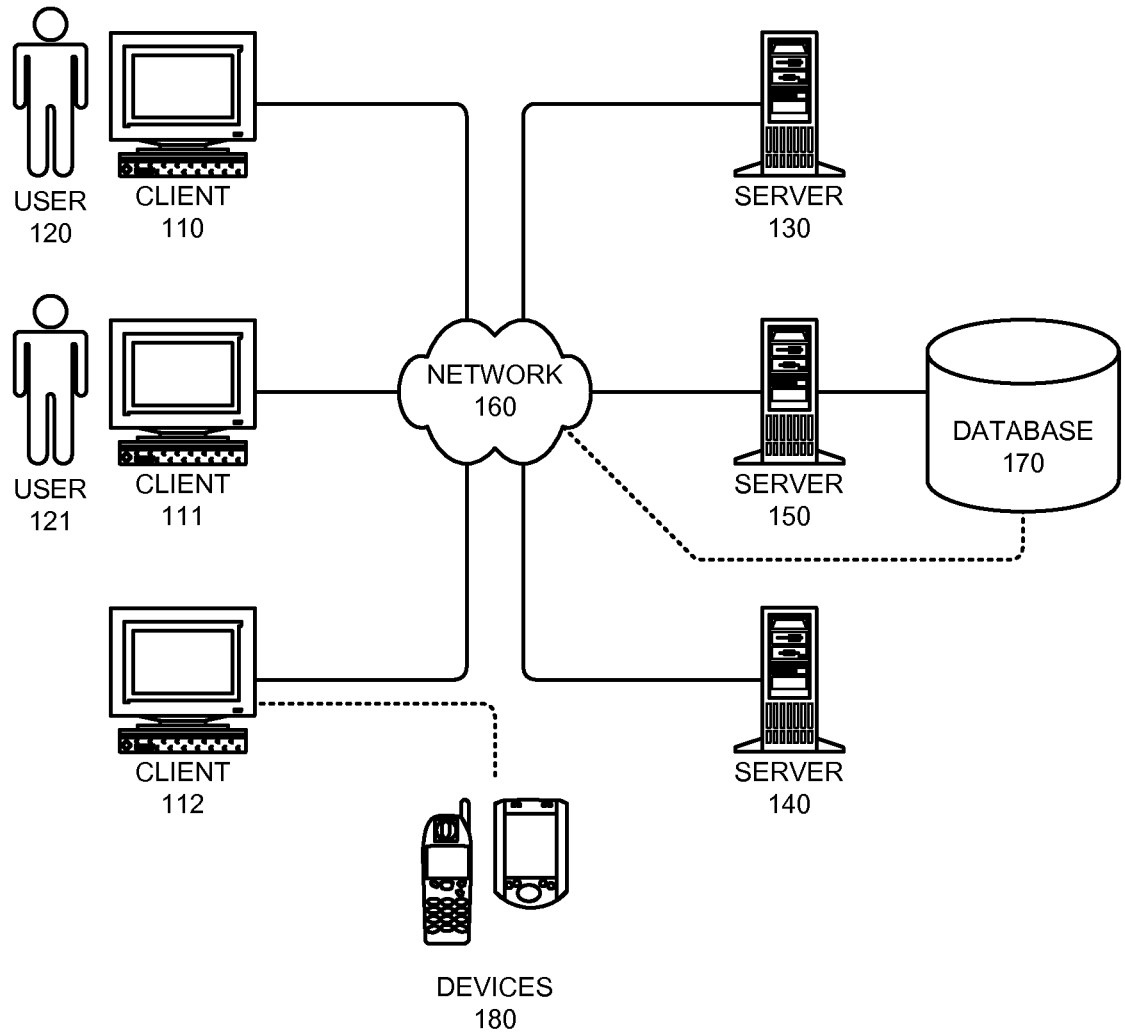
FIG. 1 illustrates a computing environment 100 in accordance with an embodiment of the present invention.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system. This includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

Overview

Some embodiments of the present invention provide a system that facilitates selecting a doctor based on an observed experience level with a condition or a procedure. During operation, the system receives from a user a selection criteria for selecting a doctor. The system also receives a medical profile for the user. Next, the system receives from a third-party a plurality of doctors' profiles. Then, the system ranks the plurality of doctors' profiles into a ranked list based on the selection criteria and conditions within the medical profile. Finally, the system sends the ranked list to the user.

In some embodiments of the present invention, the selection criteria can include: a geographic location, an offset from a geographic location, a healthcare plan, a healthcare provider organization, an in-network flag that indicates if a potential doctor is in the user's healthcare network, a time indicator that indicates if a potential doctor is available at the indicated time, a new-patient indicator indicating if a potential doctor is accepting new patients, a satisfaction rating, an amenities rating, a transportation rating, a dispute rating, a procedure cost, a recency rating, and an experience rating.

For example, the selection criteria could include any doctor within 5 miles of Dayton, Ohio, or any doctor that has an office that is easily reachable by public transportation, or any doctor who has performed a certain procedure within the last six months. The selection criteria can also include a feedback rating from other patients that have had the same procedure that the user requires, as well as a threshold for the number of complaints that are acceptable to the user. Note that any information that can be collected and/or quantified can be used as a selection criteria.

In some embodiments of the present invention, the medical profile can include: a list of medications used by the user, a history of past procedures for the user, a physical condition of the user, a race of the user, an age of the user, a sex of the user, and a religious affiliation of the user.

In some embodiments of the present invention, each profile in the plurality of doctors' profiles can include: a geographic location, a healthcare plan, a healthcare provider organization, a time indicator that indicates when a doctor is available, a new-patient indicator indicating if a doctor is accepting new patients, a satisfaction rating, an amenities rating, a transportation rating, a dispute rating, a recency rating, a procedure cost, and an experience rating.

In some embodiments of the present invention, the third-party can include: a patient, an insurance company, a healthcare organization, a professional organization, a government, and any organization that collects statistical information.

Information is collected from a number of sources and consolidated to create a comprehensive collection of doctors' profiles. For example, in some embodiments of the present invention, the system collects feedback from previous patients, information from healthcare providers, claims information from insurance companies, statistical information from government agencies, and information from the doctors themselves.

In some embodiments of the present invention, the plurality of doctors' profiles are stored in a database. In some embodiments of the present invention, the plurality of doctors' profiles are stored using a star schema. Note that the type of storage and the manner in which the profiles are stored is not meant to be limited to databases and star schemas. Any storage medium and any storage schema may be used for storing the doctor's profiles.

In some embodiments of the present invention, the system filters the ranked list based on at least one of the selection criteria and the medical profile. For example, the user may receive a list of doctors' profiles that is ranked by orthopedic surgeons that have performed knee surgeries in the past six months, and is then filtered to only show female doctors.

In some embodiments of the present invention, the system receives from the user a designation of a profile from the plurality of doctors' profiles. The system then sends the user additional information about a doctor associated with the profile.

In some embodiments of the present invention, the doctor can include one of: a medical doctor, a dentist, an optometrist, a therapist, a chiropractor, and anyone else who provides healthcare services to the user within the medical field.

Computing Environment

FIG. 1 illustrates a computing environment 100 in accordance with an embodiment of the present invention. Computing environment 100 includes a number of computer systems, which can generally include any type of computer system based on a microprocessor, a mainframe computer, a digital signal processor, a portable computing device, a personal organizer, a device controller, or a computational engine within an appliance. More specifically, referring to FIG. 1, computing environment 100 includes clients 110-112, users 120 and 121, servers 130-150, network 160, database 170, and devices 180.

Clients 110-112 can include any node on a network including computational capability and including a mechanism for communicating across the network.

Similarly, servers 130-150 can generally include any node on a network including a mechanism for servicing requests from a client for computational and/or data storage resources.

Users 120 and 121 can include an individual; a group of individuals; an organization; a group of organizations; a computing system; a group of computing systems; or any other entity that can interact with computing environment 100.

Network 160 can include any type of wired or wireless communication channel capable of coupling together computing nodes. This includes, but is not limited to, a local area network, a wide area network, or a combination of networks. In one embodiment of the present invention, network 160 includes the Internet. In some embodiments of the present invention, network 160 includes phone and cellular phone networks.

Database 170 can include any type of system for storing data in non-volatile storage. This includes, but is not limited to, systems based upon magnetic, optical, or magneto-optical storage devices, as well as storage devices based on flash memory and/or battery-backed up memory. Note that database 170 can be coupled to a server (such as server 150), to a client, or directly through a network.

Devices 180 can include any type of electronic device that can be coupled to a client, such as client 112. This includes, but is not limited to, cell phones, Personal Digital Assistants (PDAs), smart-phones, personal music players (such as MP3 players), gaming systems, digital cameras, portable storage media, or any other device that can be coupled to the client. Note that in some embodiments of the present invention, devices 180 can be coupled directly to network 160 and can function in the same manner as clients 110-112.

Selecting a Doctor Based on Observed Experience Levels

Figure 2:
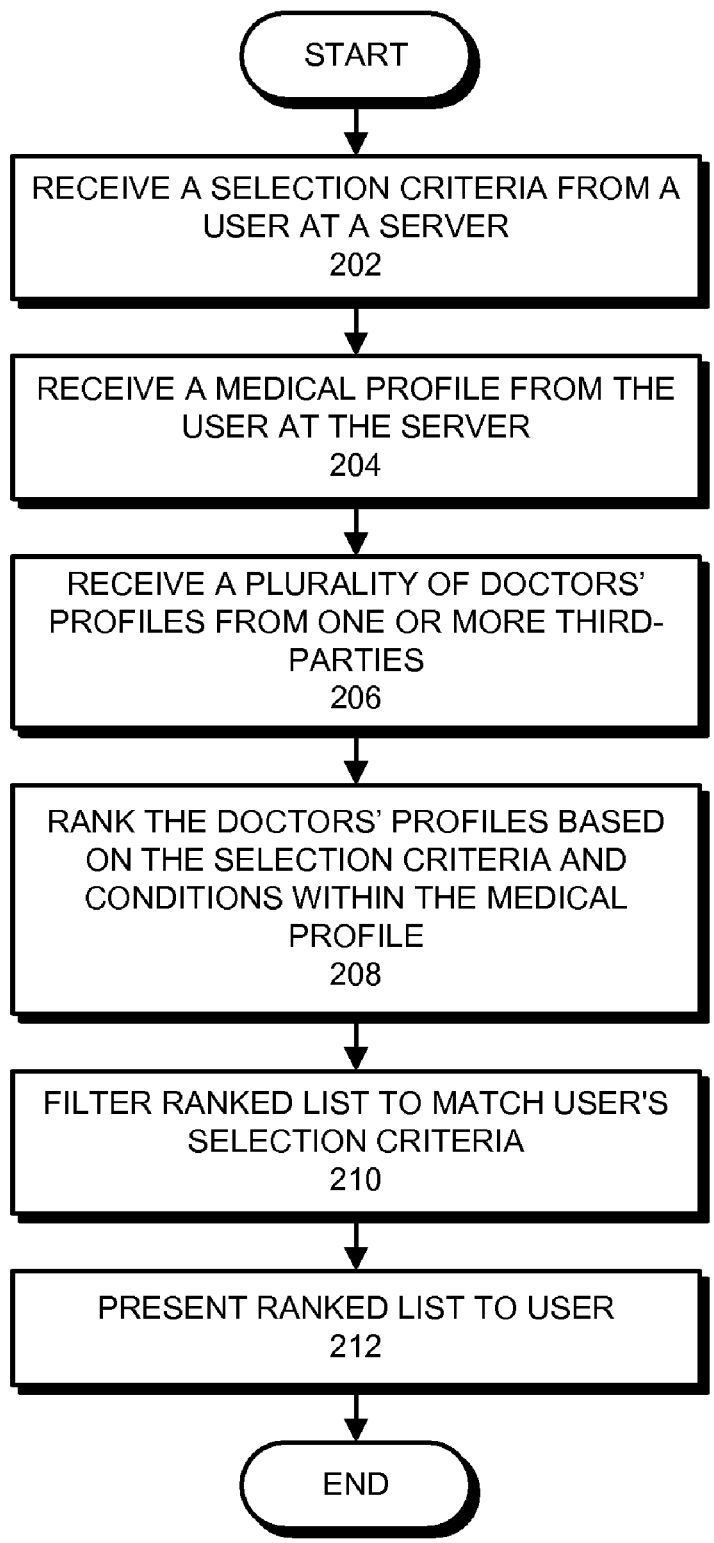
FIG. 2 presents a flow chart illustrating the process of selecting a doctor based on observed experience levels in accordance with an embodiment of the present invention.

FIG. 2 presents a flow chart illustrating the process of selecting a doctor based on observed experience levels in accordance with an embodiment of the present invention. During operation, the system receives a selection criteria from a user 120 at server 150 via a client, such as client 110 (operation 202). Note that in some embodiments of the present invention, server 150 receives the request from user 120 via devices 180. In some embodiments of the present invention, the selection criteria is received in spoken form via a phone.

In some embodiments of the present invention, user 120 is interested in selecting a dentist, while in other embodiments of the present invention, user 120 is interested in selecting a therapist. Embodiments of the present invention can be used to select any provider of healthcare services for user 120.

Next, server 150 receives a medical profile for user 120 (operation 204). Note that the system can receive the medical profile directly from user 120, or may retrieve or receive the medical profile from a third-party on user 120's behalf. For example, in one embodiment of the present invention, server 150 retrieves user 120's medical profile from user 120's doctor with user 120's permission. This medical profile can include user 120's complete medical history as well as user 120's current physical condition. For example, this medical profile may indicate that user 120 is over 100 pounds over weight and suffers from high cholesterol and hypertension.

Server 150 also receives a plurality of doctors' profiles from one or more third-parties (operation 206). Server 150 can also merge information associated with the same doctor from multiple third-parties. For example, server 150 may receive profile information directly from each doctor, such as their age, what medical school they attended, what type of practice they operate, what procedures they perform, how much their procedures cost, etc. In addition, server 150 may collect information from other sources to consolidate in each doctor's profile, such as malpractice information, insurance claim information, feedback from previous patients, such as user 121. Server 150 may also cross-check information from these various sources. For example, server 150 may verify a doctor's claim to have graduated from a specific medical school with a graduation list from the specific school.

In some embodiments of the present invention, server 150 receives streams of medical claims history for millions of patients spanning multiple healthcare plans. These streams of medical claims history are comprised of individual claims records which include: dates and times, locations, rendering and billing providers, healthcare plans, procedure codes and costs, etc. Previous patients, such as user 121, are then shown this data and can add ratings to this history to reflect relative satisfaction or dissatisfaction with the nature of the provided services. User 121 can also add ratings on other elements, such as waiting room amenities, ease of parking, etc.

Server 150 can also note the dispute incident rate for each doctor for each type of procedure. The data in this medical claims history can be processed via analytics to segment the medical claims history into episodes or conditions. For example, one segment can relate to "knee surgeries". Note that segments can overlap. Note that this information can be collected and maintained without identifying the specific users that received the procedures.

Next, server 150 ranks the doctors' profiles based on the selection criteria and conditions within the medical profile (operation 208). For example, user 120 may want to view all of the doctors within 25 miles of zip code 95901 that have repaired a torn meniscus, ranked in order of customer satisfaction. Server 150 may also filter the list to further match user 120's desires (operation 210). For example, server 150 may filter the list to exclude male doctors, or doctors that have not performed the procedure on patients that have similar conditions as user 120 as noted in user 120's medical profile.

Finally, server 150 presents the ranked and filtered list to user 120 (operation 212). Note that the system may then facilitate scheduling an appointment for user 120 based on which doctor user 120's selects from the ranked and filtered list. In some embodiments of the present invention, server 150 sends user 120 the ranked and sorted list of doctor's profiles via a web application executing on client 110. In another embodiment of the present invention, server 150 emails the ranked and sorted list to user 120, while in another embodiment of the present invention, server 150 prepares a printed version of the ranked and filtered list of doctors' profiles and mails it to user 120.

Server 150 may store the plurality of doctor's profiles in a database, such as database 170. In some embodiments of the present invention, server 150 stores the plurality of doctors' profiles in a star schema. Note that any storage method or storage schema may be used.

Server 150 may also save user 120's ranked and sorted list of doctors' profiles to facilitate subsequent searches. Note that in addition to saving the ranked and filtered list, server 150 may also save the search and filtering criteria to automatically regenerate the ranked and filtered list of doctors' profiles when user 120 requests a new copy of the list.

In one embodiment of the present invention, server 150 saves user 120's selection criteria, and automatically generates a new ranked and filtered list every time the plurality of doctors' profiles changes in a manner that would result in a different ranking of the doctors in the list. In addition, user 120 may receive notifications from server 120 is information related to doctor's on user 120's list changes. This may include indication if the change is a potentially negative or positive change. For example, the server 150 may notify user 120 if a doctor on user 120's list receives a new malpractice claim.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for facilitating the selection of a doctor based on an observed experience level with a condition or a procedure, the method comprising:
   receiving, in a computer system, a selection criteria from a user for selecting a doctor;
   saving the selection criteria received from the user in the computer system;
   receiving a medical profile for the user; receiving doctor profiles for a plurality of doctors;
   receiving additional information for each doctor from multiple third-parties;
   receiving a plurality of insurance claims for a plurality of customers from a plurality of insurance plans;
   determining a dispute incident rate for each doctor for each type of medical procedure based on the received insurance claims;
   merging information for each doctor with the dispute incident rate;
   consolidating the merged information into the profile for each doctor;
   generating a ranked and filtered list of the doctors by ranking the profiles for the doctors based on the selection criteria from the user and the dispute incident rate within the medical profile for the user;
   in response to changes in doctor profiles, automatically generating a new ranked and filtered list; and
   sending the new ranked and filtered list to the user.

2. The method of claim 1, wherein the selection criteria include at least one of:
   a geographic location;
   an offset from a geographic location;
   a healthcare plan;
   a healthcare provider organization;
   an in-network flag that indicates if a potential doctor is in the user's healthcare network;
   a time indicator that indicates if a potential doctor is available at the indicated time;
   a new-patient indicator indicating if a potential doctor is accepting new patients;
   a satisfaction rating;
   an amenities rating;
   a transportation rating;
   a dispute rating;
   a procedure cost;
   a recency rating; and
   an experience rating.

3. The method of claim 1, wherein the medical profile includes at least one of:
- a list of medications used by the user;
- a history of past procedures for the user;
- a physical condition of the user;
- a race of the user;
- an age of the user;
- a sex of the user; and
- a religious affiliation of the user.

4. The method of claim 1, wherein a doctor's profile includes at least one of:
- a geographic location;
- a healthcare plan;
- a healthcare provider organization;
- a time indicator that indicates when a doctor is available;
- a new-patient indicator indicating if a doctor is accepting new patients;
- a satisfaction rating;
- an amenities rating;
- a transportation rating;
- a dispute rating;
- a recency rating;
- a procedure cost; and
- an experience rating.

5. The method of claim 1, wherein the third parties include at least one of:
- a patient;
- an insurance company;
- a healthcare organization;
- a professional organization;
- a government; and
- any organization that collects statistical information.

6. The method of claim 1, wherein the doctor profiles are stored in a database.

7. The method of claim 6, wherein the doctor profiles are stored using a star schema.

8. The method of claim 1, further comprising:
- receiving from the user a selection of a doctor profile; and
- sending the user additional information about the doctor associated with the profile.

9. The method of claim 1, wherein the doctor is at least one of:
- a medical doctor;
- a dentist;
- an optometrist;
- a therapist;
- a chiropractor; and
- anyone else who provides healthcare services to the user within the medical field.

10. A computer-readable storage medium storing instructions that when executed by a computer cause the computer to perform a method for facilitating the selection of a doctor based on an observed experience level with a condition or a procedure, the method comprising:
- receiving, in a computer system, a selection criteria from a user for selecting a doctor;
- saving the selection criteria received from the user in the computer system;
- receiving a medical profile for the user; receiving doctor profiles for a plurality of doctors;
- receiving additional information for each doctor from multiple third-parties;
- receiving a plurality of insurance claims for a plurality of customers from a plurality of insurance plans;
- determining a dispute incident rate for each doctor for each type of medical procedure based on the received insurance claims;
- merging information for each doctor with the dispute incident rate;
- consolidating the merged information into the profile for each doctor;
- generating a ranked and filtered list of the doctors by ranking the profiles for the doctors based on the selection criteria from the user and the dispute incident rate within the medical profile for the user;
- in response to changes in doctor profiles, automatically generating a new ranked and filtered list; and
- sending the new ranked and filtered list to the user.

11. The computer-readable storage medium of claim 10, wherein the selection criteria include at least one of:
- a geographic location;
- an offset from a geographic location;
- a healthcare plan;
- a healthcare provider organization;
- an in-network flag that indicates if a potential doctor is in the user's healthcare network;
- a time indicator that indicates if a potential doctor is available at the indicated time;
- a new-patient indicator indicating if a potential doctor is accepting new patients;
- a satisfaction rating;
- an amenities rating;
- a transportation rating;
- a dispute rating;
- a procedure cost;
- a recency rating; and
- an experience rating.

12. The computer-readable storage medium of claim 10, wherein the medical profile includes at least one of:
- a list of medications used by the user;
- a history of past procedures for the user;
- a physical condition of the user;
- a race of the user;
- an age of the user;
- a sex of the user; and
- a religious affiliation of the user.

13. The computer-readable storage medium of claim 10, wherein a doctor's profile includes at least one of:
- a geographic location;
- a healthcare plan;
- a healthcare provider organization;
- a time indicator that indicates when a doctor is available;
- a new-patient indicator indicating if a doctor is accepting new patients;
- a satisfaction rating;
- an amenities rating;
- a transportation rating;
- a dispute rating;
- a recency rating;
- a procedure cost; and
- an experience rating.

14. The computer-readable storage medium of claim 10, wherein the third-parties include at least one of:
- a patient;
- an insurance company;
- a healthcare organization;
- a professional organization;
- a government; and
- any organization that collects statistical information.

15. The computer-readable storage medium of claim 10, wherein the doctor profiles are stored in a database.

16. The computer-readable storage medium of claim 15, wherein the doctor profiles are stored using a star schema.

17. The computer-readable storage medium of claim 10, wherein the method further comprises:
receiving from the user a selection of a doctor profile; and
sending the user additional information about the doctor associated with the profile.

18. The computer-readable storage medium of claim 10, wherein the doctor is at least one of:
a medical doctor;
a dentist;
an optometrist;
a therapist;
a chiropractor; and
anyone else who provides healthcare services to the user within the medical field.

19. An apparatus configured for facilitating the selection of a doctor based on an observed experience level with a condition or a procedure, comprising:
a processor;
a memory;
a receiving mechanism configured to receive from a user a selection criteria for selecting a doctor;
receive a medical profile for the user;
receive doctor profiles for a plurality of doctors;
receive additional information for each doctor from multiple third-parties; and
receive a plurality of insurance claims for a plurality of customers from a plurality of insurance plans;
a saving mechanism configured to save the selection criteria received from the user;
a determination mechanism configured to determine a dispute incident rate for each doctor for each type of procedure from the received insurance claims;
a merging mechanism configured to merge information for each doctor with the dispute incident rate;
a consolidating mechanism configured to consolidate the merged information into the profile for each doctor;
a generating mechanism configured to generate a ranked and filtered list of the doctors by ranking the profiles for the doctors based on the selection criteria from the user and the dispute incident rate within the medical profile for the user;
wherein the generating mechanism is further configured to automatically generating a new ranked and filtered list in response to changes in doctor profiles; and
a delivery mechanism configured to send the new ranked and filtered list to the user.

20. A method for facilitating the selection of professional based on an observed experience level of the professional, the method comprising:
receiving, in a computer system, a selection criteria for selecting the professional from a user;
saving, in the computer system, the selection criteria received from the user;
receiving, in the computer system, a user profile for the user;
receiving, in the computer system, professional profiles for a plurality of professionals;
receiving additional information associated with each professional from multiple third-parties;
receiving a plurality of insurance claims for a plurality of customers from a plurality of insurance plans;
determining a dispute incident rate for each professional for each type of procedure based on the received insurance claims;
merging the information for each professional with the dispute incident rate;
consolidating the merged information into the profile for each professional;
generating, in the computer system, a ranked and filtered list of the professionals by ranking the profiles for the professionals based on the selection criteria from the user and the dispute incident rate within the user profile;
in response to changes in profiles of the professionals, automatically generating a new ranked and filtered list; and
sending the new ranked and filtered list from the computer system to the user.

21. A computer-readable storage medium storing instructions that when executed by a computer cause the computer to perform a method for facilitating the selection of professional based on an observed experience level of the professional, the method comprising:
receiving from a user a selection criteria for selecting the professional;
saving the selection criteria received from the user;
receiving a user profile for the user;
receiving professional profiles for a plurality of professionals;
receiving additional information associated with each professional from multiple third-parties;
receiving a plurality of insurance claims for a plurality of customers from a plurality of insurance plans;
determining a dispute incident rate for each professional for each type of procedure based on the received insurance claims;
merging the information for each professional with the dispute incident rate;
consolidating the merged information into the profile for each professional;
accessing a third-party database for data used to verify information associated with each professional;
verifying information associated with each professional based on the accessed data; generating a ranked and filtered list of the professionals by ranking the profiles for the professionals based on the selection criteria from the user and the dispute incident rate within the user profile;
in response to changes in profiles of the professionals, automatically generating a new ranked and filtered list; and
sending the new ranked and filtered list from the computer system to the user.

* * * * *